United States Patent [19]

Haines et al.

[11] Patent Number: 5,563,333
[45] Date of Patent: Oct. 8, 1996

[54] METHOD AND APPARATUS FOR CORE FLOODING STUDIES

[76] Inventors: Hiemi K. Haines, 6665 E. Jamison Ave., Englewood, Colo. 80112; Gary R. Kennedy, 1620 S. Wolff St., Denver, Colo. 80219; Richard D. Favinger, 2764 E. Euclaid Pl., Littleton, Colo. 80121

[21] Appl. No.: 376,593

[22] Filed: Jan. 20, 1995

[51] Int. Cl.⁶ .................................................. G01N 3/00
[52] U.S. Cl. ................................................................ 73/38
[58] Field of Search ...................................... 73/38, 865.6

[56] References Cited

U.S. PATENT DOCUMENTS

| | | | |
|---|---|---|---|
| 446,248 | 2/1891 | Cooper . | |
| 934,833 | 9/1909 | Parker . | |
| 2,345,935 | 4/1944 | Hassler | 73/38 |
| 2,692,856 | 10/1954 | Litman | 252/8.5 |
| 2,705,418 | 4/1955 | Reichertz et al. | 73/38 |
| 3,329,006 | 7/1967 | Silken | 73/38 |
| 3,487,994 | 1/1970 | Moore | 233/26 |
| 3,839,899 | 10/1974 | McMillen | 73/38 |
| 4,342,419 | 8/1982 | Conway | 233/1 A |
| 4,671,102 | 6/1987 | Vinegar | 73/61.1 R |
| 4,817,423 | 4/1989 | Christiansen | 73/153 |
| 4,830,493 | 5/1989 | Giebeler | 356/328 |
| 4,919,537 | 4/1990 | Giebeler | 356/328 |
| 5,325,723 | 7/1994 | Meadows et al. | 73/38 |

*Primary Examiner*—Robert Raevis
*Attorney, Agent, or Firm*—Jack L. Hummel; Jack E. Ebel

[57] ABSTRACT

An apparatus and process for observing fluid replacement in core samples while simulating subsurface reservoir conditions, including oil composition, temperature, fluid pressure, and overburden pressure. Overburden pressure is applied to a core sample placed in the apparatus, and the core sample is saturated with a core saturating fluid at a pressure greater than the bubble point pressure of the core saturating fluid. One or more replacement fluids are provided in fluid communication with the core sample and at the same pressure as the core saturating fluid pressure. The apparatus is placed in a centrifuge and spun, and the extent and rate of replacement of the core saturating fluid in the core by a replacement fluid can be observed.

7 Claims, 6 Drawing Sheets

5,563,333

METHOD AND APPARATUS FOR CORE FLOODING STUDIES

FIELD OF THE INVENTION

This invention relates generally to the use of a centrifuge to simulate gravity in core flooding studies, and in particular to a method and apparatus for simulating reservoir conditions, including fluid composition, temperature, fluid pressure, and overburden pressure.

BACKGROUND OF THE INVENTION

One way to predict the rate and extent of gravity displacement of fluids in a subterranean hydrocarbon reservoir is to study the behavior of the fluids in core samples obtained from the reservoir. In the laboratory, a centrifuge can be used to increase the rate of fluid replacement in core samples by substituting centrifugal force for gravity. In centrifuge experiments, core samples are saturated with oil of the type found in the reservoir, and the cores are then contacted by one or more flooding fluids while the samples are spun in a centrifuge.

As found in hydrocarbon reservoirs, oil generally contains a significant quantity of dissolved volatile components. When the oil is maintained at ambient laboratory conditions, the volatile components evaporate, leaving what is known as "dead oil". One problem encountered in simulating a process which is to occur in a reservoir containing oil with a substantial fraction of volatile components is that when core samples are saturated with dead oil, the simulation may not indicate what would happen in the reservoir. Thus, a better simulation of the displacement process is possible if the core samples are saturated with oil that contains the volatile components. This oil can be "recombined", or mixed from dead oil and volatile components equivalent to those which were previously lost. However, the saturation and displacement operations must be carried out under reservoir temperature and pressure conditions, or the volatile components will again be lost.

Thus, there is a need for a means to saturate core samples with recombined oil under reservoir temperature and pressure conditions. There is also a need for a means to maintain the core samples under reservoir temperature and pressure conditions during centrifuge studies of fluid replacement in the cores.

Accordingly, a primary object of the present invention is to provide a method for performing centrifuge studies of fluid displacement in cores under simulated reservoir overburden, temperature, and pressure conditions.

Another object of the present invention is to provide a means for performing centrifuge studies of fluid displacement in cores under simulated reservoir overburden, temperature, and pressure conditions.

SUMMARY OF THE INVENTION

To achieve the foregoing and other objects, and in accordance with the purposes of the present invention, as embodied and broadly described herein, one characterization of the present invention comprises a method for studying fluid replacement in core samples under reservoir temperature and pressure conditions. Overburden pressure is provided to a core sample, and the core sample is loaded into a centrifuge bucket so that the core has a proximal end and a distal end. The core sample is flooded with a core flooding fluid having a substantial volatile fraction and bubble point pressure less than the reservoir pressure. At least one replacement fluid is supplied to at least one end of the core sample, and reservoir pressure is applied to the core saturating fluid and the at least on replacement fluid. The bucket is heated to the reservoir temperature. The bucket is spun in a centrifuge while maintaining the core flooding fluid and the at least one replacement fluid at the reservoir temperature and fluid pressure. As a result of spinning the bucket, the at least one replacement fluid is imbibed into the core sample, and the core flooding fluid replaced in the core sample. The volumes of replaced core flooding fluid and the at least one replacement fluid are determined.

Another embodiment of the present invention comprises a centrifuge bucket assembly for use in a centrifuge to study fluid replacement in core samples. The assembly comprises a bucket, an end cap, a core holder, and a means for supplying overburden pressure to said core holder. The bucket has an open proximal end, a distal end wall, a distal multiple valve assembly mounted in a distal valve socket in the end wall, a distal collection vessel in fluid communication with the distal valve socket, and a proximal collection vessel. The end cap is capable of being secured to the proximal end of the centrifuge bucket. A proximal multiple valve assembly is mounted in a proximal valve socket in the cap, and a passage provides fluid communication between the proximal valve socket and the proximal collection vessel. The core sample holder contains a core sample while overburden pressure is applied to the core sample. The core sample holder comprises an outer wall, a core drain cap, a distal end plate, a resilient sleeve, an annulus between the outer wall and the sleeve, and a valve for introducing a fluid at overburden pressure into the annulus and maintaining pressure within the annulus. The sample holder is also capable of being placed inside said bucket so that the core sample has a proximal end in fluid communication with the proximal collection vessel and a distal end in fluid communication with the distal collection vessel. The proximal collection vessel can be sealingly mounted substantially between the proximal end of the core sample and the end cap, and the distal collection vessel can be sealingly mounted substantially between the distal end of the core sample and the distal end wall of the bucket. A means is also provided for supplying overburden pressure to the core holder. The apparatus is capable of operation under conditions simulating subsurface hydrocarbon reservoir conditions, including fluid compositions, temperature, fluid pressure, and overburden pressure.

Another characterization of the present invention is an apparatus for studying fluid replacement in core samples. The apparatus is capable of operation under conditions simulating subsurface hydrocarbon reservoir conditions, including fluid compositions, temperature, fluid pressure, and overburden pressure. It comprises a bucket for use in a centrifuge, a spacer within the bucket separating the interior space into a core chamber and a fluid collection chamber, and a cap containing at least two valve assemblies providing for fluid flow through the cap. The bucket has a side wall, a closed end, and an open end that define an interior space. First, second, and third passages through the side wall connect a first bucket valve assembly, a second bucket valve assembly, and a third bucket valve assembly to the interior space, respectively. The spacer is adjacent the first, second, and third passages and comprises means for providing fluid communication between the core chamber and the first passage and means for providing fluid communication between the fluid collection chamber and the second and third passages. The cap contains at least two valve assemblies providing for fluid flow through the cap.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENT

Figure 1:
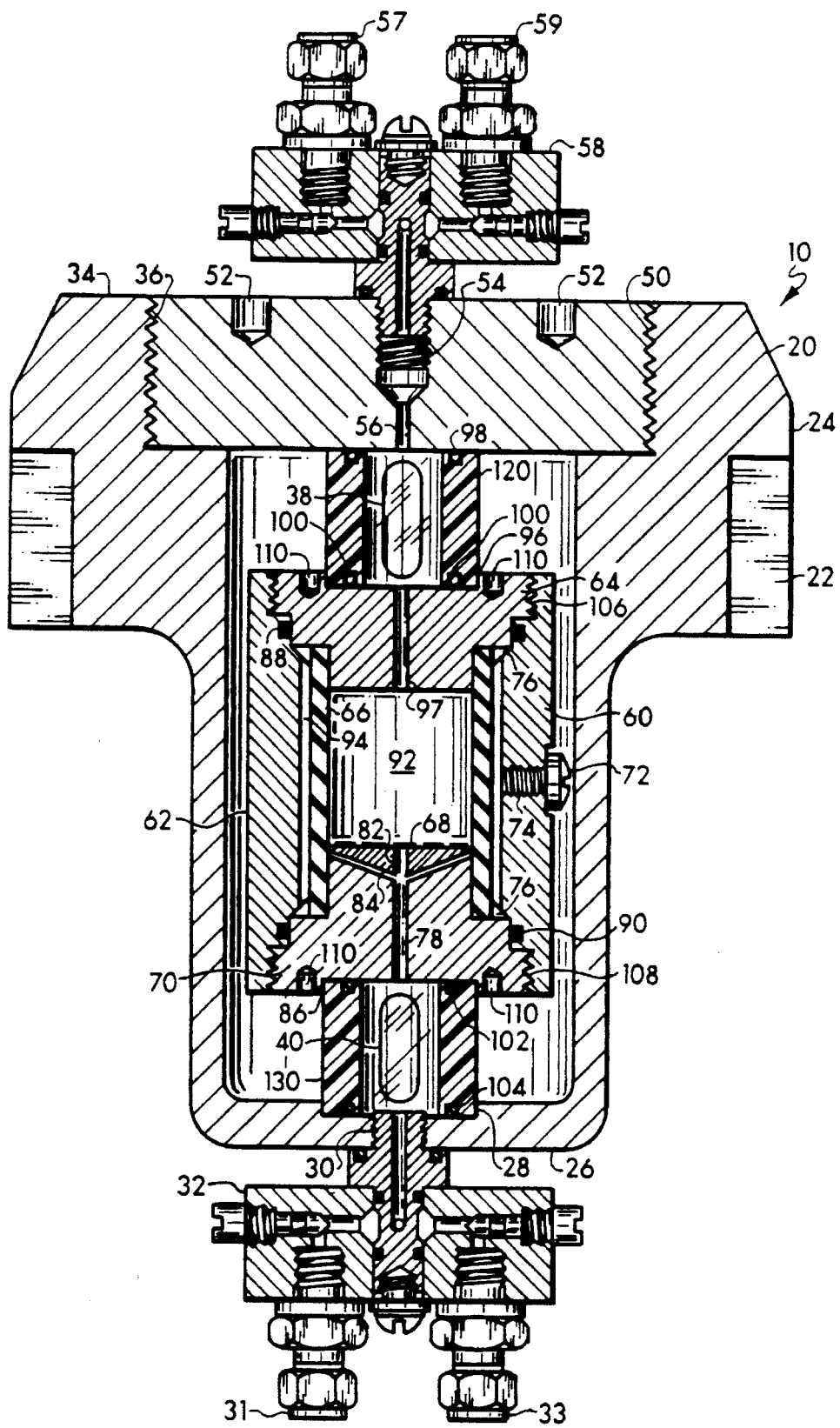
FIG. 1 is a cross section from proximal to distal of one embodiment of a centrifuge bucket assembly of the present invention, showing a bucket, an end cap, a core holder, proximal and distal fluid collection vessels, and proximal and distal valve assemblies.

One characterization of the present invention comprises a method for determining the rate and extent of fluid replacement, under reservoir pressure, temperature, and overburden conditions, in a core sample that is saturated with recombined oil having a known bubble point. The method utilizes a centrifuge bucket assembly for use in a centrifuge, such as a swinging bucket centrifuge.

A swinging bucket centrifuge has a rotor with at least two arms spaced symmetrically about a central axis, and each arm terminates in two pivot pins. A centrifuge bucket hangs and pivots on each pair of pins. As the rotational velocity of the rotor about its central axis increases, centrifugal force causes the buckets to pivot on the pins until, at a sufficiently high rotation rate, the long axes of the buckets are perpendicular to the axis of rotation. In other centrifuges, the buckets are rigidly attached to the ends of the rotor arms and do not pivot. In the following discussion, the directional references describe positions relative to the rotor axis in the centrifuge. The term "proximal" means closer to the centrifuge rotor shaft, and "distal" means farther away from the rotor shaft.

In the method of the present invention, a core sample is initially saturated with a core saturating fluid and then subjected to overburden pressure. "Core saturating fluid" refers to a fluid used to saturate, or fill the pore spaces within, a core sample. The core could be saturated with any fluid as long as the fluid does not react chemically with the core. Although the saturating fluid may be air, the preferred core saturating fluid is a liquid, such as recombined oil, separator oil, synthetic oil, or brine. An overburden fluid is utilized to provide overburden pressure to the core sample. The overburden fluid does not contact the core directly, and it may be any fluid which can be handled easily and which does not react with or corrode the apparatus with which it is used under the temperature and pressure conditions of the experiment.

A core flooding fluid is then caused to flow through the core under reservoir fluid pressure and temperature so that the flooding fluid displaces the saturating fluid from the void spaces within the core. As utilized in the present invention, core flooding fluid may have a substantial volatile component. Examples of core flooding fluids are live oil, as collected from a well, and recombined oil, or dead oil to which the volatile components have been restored. The fluid pressure should be greater than the bubble point pressure of the flooding fluid at the reservoir temperature to prevent escape of the volatile component.

After the core sample is placed in a centrifuge bucket so that the core has a proximal end and a distal end, the core sample is heated and contacted by one or more replacement fluids while being spun in a centrifuge. Examples of replacement fluids are water, brine, aqueous surfactant solutions, and gaseous hydrocarbons. The fluid or fluids may be supplied to either the proximal or the distal end of the core, or both, for studying two-phase relative permeability, three-phase relative permeability, cocurrent flow, or countercurrent flow. Table I lists possible combinations of fluids for use in accordance with this invention. If a proximal replacement fluid is utilized, it is preferably is more dense than the core saturation fluid. If a distal replacement fluid is utilized, it preferably is less dense than the core saturation fluid. As the sample spins, reservoir temperature and pressure conditions are maintained. Some of the replacement fluid or fluids is imbibed into the core sample and replaces the core flooding fluid in the core, and the core flooding fluid collects in one or more fluid collection vessels.

TABLE I

| Proximal Replacement Fluid | Core Flooding Fluid | Distal Replacement Fluid |
|---|---|---|
| gas | oil | gas |
| water | oil | water |
| water | gas | oil |
| water | oil | gas |
| oil | water | gas |
| oil | water + gas | oil |
| gas | water + oil | gas |
| water | oil + gas | water |
| water | water + oil + gas | water |

While the sample is spinning, the fluid volumes in the vessel or vessels are observed optically or by any other method known to those skilled in the art. Observations may be made periodically or continuously while the bucket is spinning. The measurements may be obtained manually or with an automated system, such as a camera linked to a computer system. Further, the measurements may be recorded as a function of time and/or rotational speed.

Referring to FIG. 1, one embodiment of a centrifuge bucket assembly of the present invention is shown generally as 10. The assembly comprises a bucket 20, an end cap 50, a core holder 60, a proximal collection vessel 120, and a distal collection vessel 130. The embodiment also comprises means for supplying a fluid at overburden pressure to the core holder, shown generally as 150 in FIG. 2.

Grooves 22 are cut into flange 24 on bucket 20 to allow the bucket to hang and pivot on the pivot pins of the centrifuge rotor. Distal end 26 of bucket 20 has a recess 28 for receiving distal collection vessel 130. Distal valve socket 30 and distal valve assembly 32, shown as a dual assembly comprising valves 31 and 33, provide for fluid passage through the distal end 26 of bucket 20. Alternatively, end 26 could include two or more valve sockets and valve assemblies. The proximal end 34 of bucket 20 is adapted for receiving end cap 50, shown with screw threads 36. Alternatively, end cap 50 could be secured to bucket 20 by bolts passing through end cap 50 and flange 24. The fluid collection vessels 120 and 130 may be transparent, and opposing pairs of windows 38 and 40 allow fluid levels within the vessels to be monitored. As is apparent to one skilled in the art, two or more pairs of windows could be used to monitor the fluid levels within each vessel.

End cap 50 is adapted to fit into or onto the proximal end 32 of bucket 20. As shown, end cap 50 screws into proximal end 34 of bucket 20. A spanner wrench may be utilized with holes 52 to screw or unscrew end cap 50. Proximal valve socket 54 and passage 56 provide fluid communication between the interior and the exterior of bucket 20. A proximal valve assembly 58, shown as a dual valve assembly comprising valves 57 and 59, may be inserted into valve socket 54. Alternatively, two or more valve assemblies could be mounted in separate sockets in cap 50.

Figure 3:
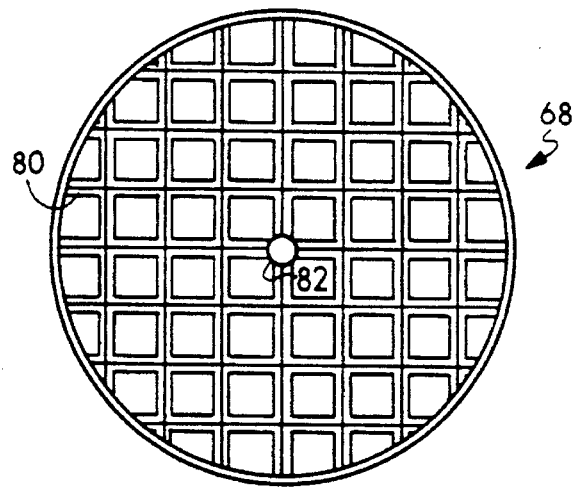
FIG. 3 is a view of the proximal surface of a core drain cap of the embodiment of FIG. 1.
Figure 4:
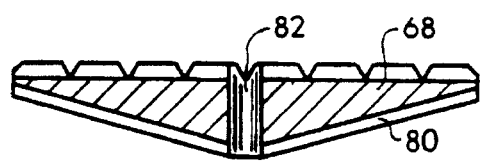
FIG. 4 is a cross section from proximal to distal through the core drain cap of FIG. 3.
Figure 5:
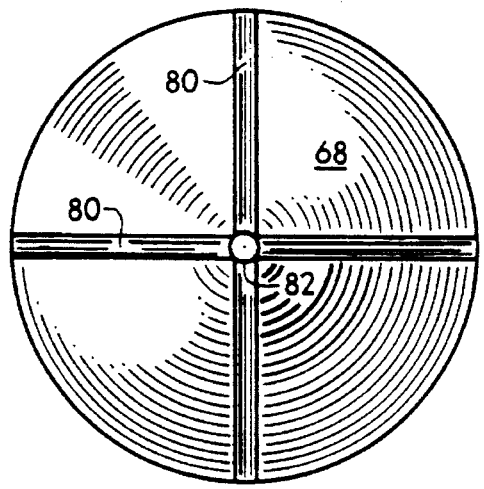
FIG. 5 is a view of the distal surface of the core drain cap of FIG. 3.

Core holder 60 comprises an outer wall 62, a proximal end plate 64, an inner core sleeve 66, a core drain cap 68, and distal end plate 70. O-seal screw 72 has a conventional screw head and seals passage 74 through outer wall 62. Inner core sleeve 66, made from a resilient material, is secured between outer wall 62, proximal end plate 64, and distal end plate 70 by retainers 76. Bore 97 provides for fluid communication through proximal end plate 64. Core drain cap 68 has a cylindrical wall between proximal and distal surfaces and is adapted to collect fluid and facilitate fluid flow into bore 78. As shown in FIGS. 3, 4, and 5, grooves 80 are carved into the wall and surfaces of core drain cap 68, and a central bore 82 passes through the interior of the drain cap. The proximal surface of distal end plate 70 is a conical recess 84, and the distal surface of the end plate contains an additional recess 86 to receive the proximal end of distal collection vessel 130. Bore 78 provides a fluid passage through end plate 70. O-rings 88 and 90 provide seals between outer wall 62 and proximal end plate 64 and between wall 62 and distal end plate 70, respectively. A core chamber 92 is inside sleeve 66, and an annular overburden fluid chamber 94 is between sleeve 66 and outer wall 62. A recess 96 in proximal end plate 64 accommodates collection vessel 120, and bore 97 provides for fluid flow through end plate 64. When the bucket 20, collection vessels 120 and 130, core holder 60, and end cap 50 are assembled as shown in FIG. 1, O-rings 98, 100, 102, and 104 provide additional seals.

Figure 2:
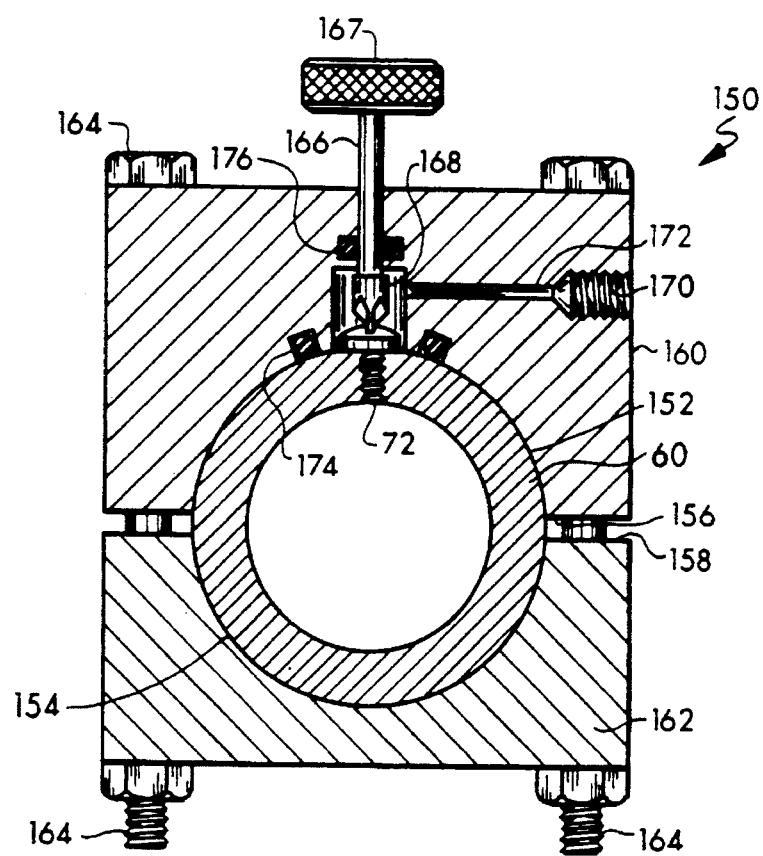
FIG. 2 is a cross section through an apparatus for providing overburden pressure to the core holder of the embodiment of FIG. 1.

FIG. 2 shows an apparatus 150 for providing overburden pressure to a core sample in core holder 60. Recesses 152 and 154 are carved into interior surfaces 156 and 158 of upper and lower plates 160 and 162, respectively. Bolts 164 pass through holes (not shown) in plates 160 and 162 and clamp the plates together, forming a chamber between the plates to accommodate core holder 60. As shown, nuts are used with the bolts 164. Alternatively, bolts 164 could screw directly into female threaded holes in plate 162 or 164, or more than two plates could be utilized. Core sleeve 66 is not shown in FIG. 2. Screw driver 166 has a handle 167 for rotating the screw driver and terminates in a screw driver head 168, shown as a phillips head, and is capable of rotating O-seal screw 72 in core holder 60. Alternatively, any screw driver compatible with the head of screw 72 could be utilized. Valve socket 170 accommodates a valve, not shown, for use in controlling fluid flow through passage 172. O-ring 174 provides a seal between upper plate 160 and outer wall 62, and O-ring 176 provides a seal between upper plate 160 and the shaft of screw driver 166.

The apparatus of FIGS. 1–5 may be used in the method of the present invention for core flooding experiments using recombined oil. A core sample is initially saturated with a saturating fluid, and core sample holder 60 is assembled with the saturated core sample in core chamber 92 inside core sleeve 66. End plates 64 and 70 are secured to the ends of outer wall 62 so as to seal the ends of overburden fluid chamber 94. For example, the end plates may be screwed with screw threads 106 and 108 into the ends of wall 62 using a spanner wrench in holes 110. O-seal screw 72 is left loose, providing a fluid passage along the screw threads between the exterior of outer wall 62 and overburden fluid chamber 94. With screw driver 166 loose, core holder 60 is then placed in apparatus 150 with screw driver head 168 aligned with O-seal screw 72, and bolts 164 are tightened so that O-ring 174 forms a seal around O-seal screw 72. A valve is inserted into valve socket 170 and connected to a source of overburden fluid and a backpressure regulator. The valve is opened, allowing fluid to pass through passage 172 and along the threads of O-seal screw 72 into overburden fluid chamber 94. As the pressure in chamber 94 increases to the desired overburden pressure, resilient core sleeve 66 is pressed against the core sample to form a seal with the side of the core sample. When the desired overburden pressure is reached, screw driver 166 is pushed against the head of O-seal screw 72 to engage screw driver head 168 with the head of O-seal screw 72. The overburden pressure should be greater than the bubble point pressure of the core flooding fluid to be used later to flood the core. As handle 167 is used to rotate screw driver 166, O-seal screw 72 is also tightened until it seals overburden fluid chamber 94. The valve is closed, and the overburden fluid supply is disconnected. Bolts 164 are then loosened, and core holder 60 is removed from apparatus 150.

Distal collection vessel 130 is placed inside recess 28 in the distal end of bucket 20. Core holder 60 is placed inside the bucket 20 so that the proximal end of collection vessel 130 is inserted into recess 86 in distal end plate of core holder 60. Proximal collection vessel 120 is placed in bucket 20 so that its distal end is inserted into recess 96 in proximal end plate 64, and end cap 50 is secured onto or into the proximal end of bucket 20. A fluid flow path is thus created through valve socket 54, passage 56, the interior of proximal collection vessel 120, bore 97, the core sample, bores 82 and 78, the interior of distal collection vessel 130, and valve socket 30. Valve assemblies 32 and 58 are then inserted into valve sockets 30 and 54, respectively. As is apparent to one skilled in the art, multiple valve assemblies, such as the dual valve assemblies shown in FIG. 1, can be utilized.

Valve 57 is then connected to a source of a core flooding fluid, and valve 31 is connected to a first receptacle for flushed fluids. Valves 33 and 59 are closed, and valves 31 and 57 are opened. Several pore volumes of core flooding fluid are pumped or allowed to flow through the core at a pressure selected to be greater than the bubble point of the core flooding fluid and approximately the same as the fluid pressure in the reservoir being simulated. Valves 31 and 57 are then closed, and the oil source is disconnected from valve 57. At this point in the method, the core is saturated with core flooding fluid, and proximal and distal collection vessels 120 and 130 are filled with core flooding fluid.

Valve 57 is then connected to a source of a proximal replacement fluid and a backpressure regulator, and valve 59 is connected to a second receptacle. Valves 57 and 59 are opened, and the proximal replacement fluid displaces the oil in proximal collection vessel 120. Similarly, valve 33 is connected to a source of a distal replacement fluid and a backpressure regulator, while the valve 31 remains connected to the first receptacle. Valves 31 and 33 are opened, and the distal replacement fluid displaces the oil in distal collection vessel 130. Valves 31, 33, 57, and 59 are then closed and disconnected from the fluid sources and receptacles.

The bucket is then placed in the centrifuge and spun. Centrifugal force causes the proximal and distal replacement fluids to replace the oil in the core much more rapidly than under normal gravity, allowing the effects to be observed relatively rapidly. While the bucket is spinning, the fluid volumes in each collection cup may be observed through the paired windows 38 and 40 and recorded.

Figure 6:
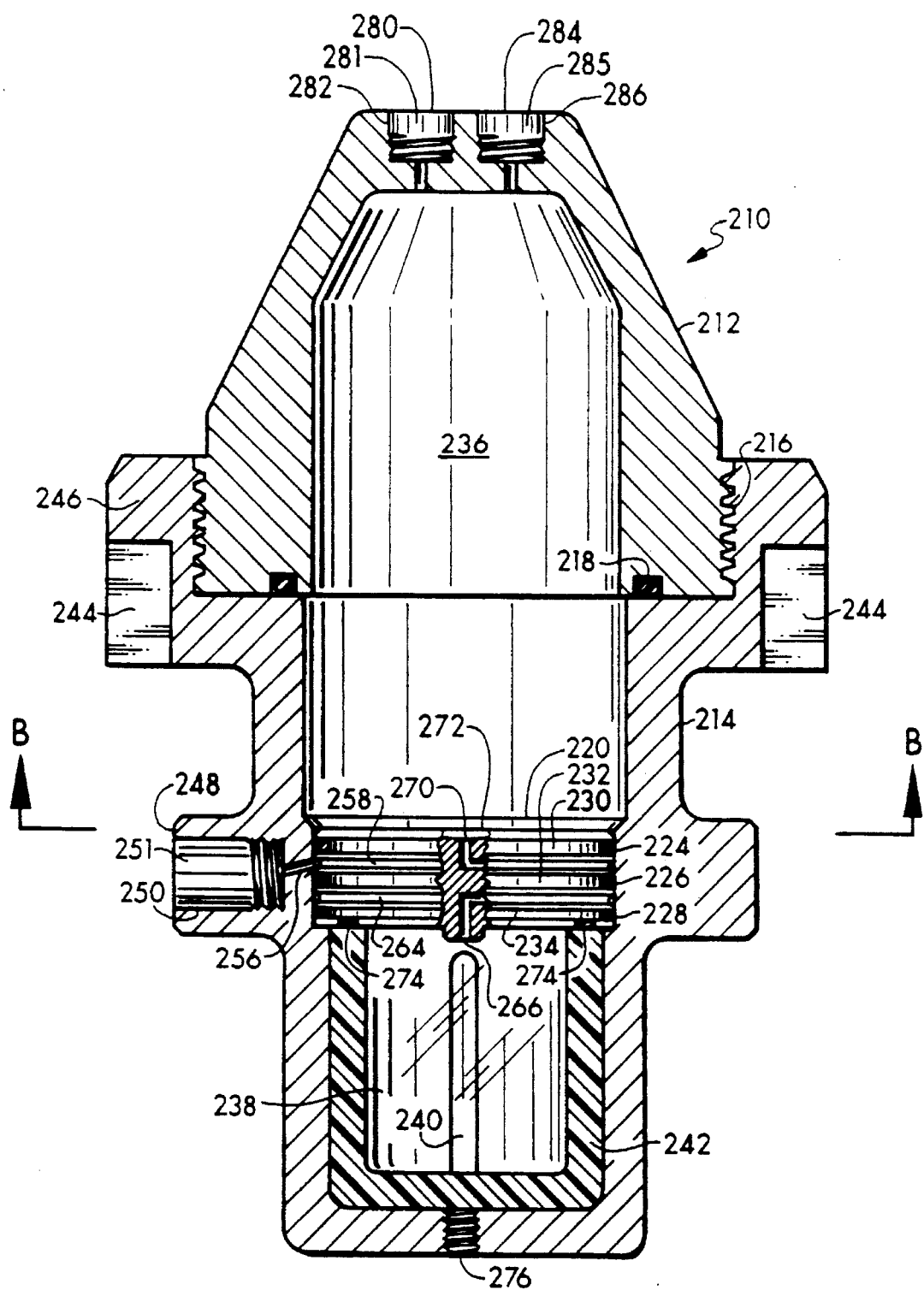
FIG. 6 is a cross section from proximal to distal of another embodiment of the centrifuge bucket assembly of the present invention, showing a bucket, a cap, a spacer, and a fluid collection vessel.

Referring to FIG. 6, another embodiment 210 of a centrifuge bucket assembly has a cap 212 which is secured onto or into bucket 214, such as with screw threads 216. An O-ring seal 218 prevents fluid leakage from the bucket. A spacer 220 and O-rings 224, 226, and 228 in O-ring grooves 230, 232, and 234 separate the interior of the bucket into a core chamber 236 and a fluid collection chamber 238. Two windows 240 on opposite sides of the distal portion of bucket 214 allow transmission of light through the fluid collection chamber 238. Inside the fluid collection chamber 238 is a fluid collection vessel 242.

Figure 7:
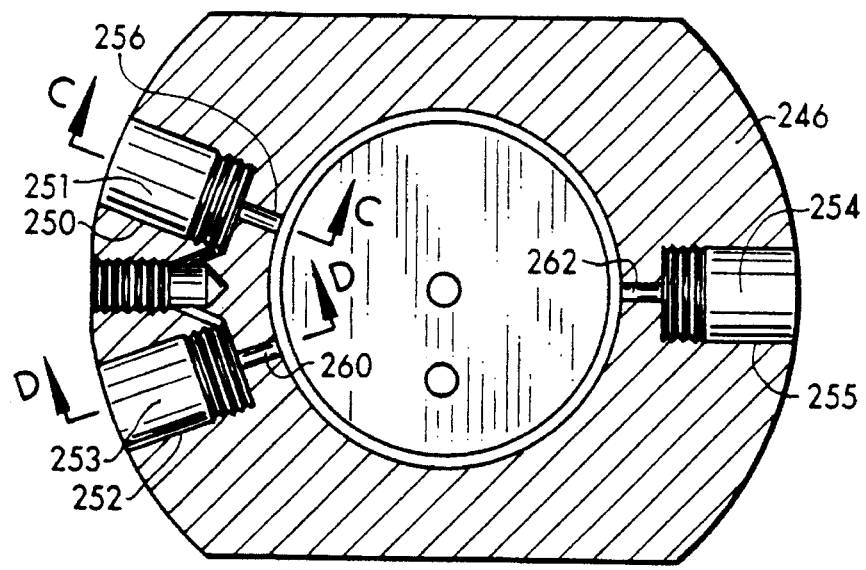
FIG. 7 is a cross section, oriented perpendicular to the section of FIG. 6, through a second flange of the centrifuge bucket assembly of FIG. 6, showing a first bucket valve socket and a second bucket valve socket.
Figure 8:
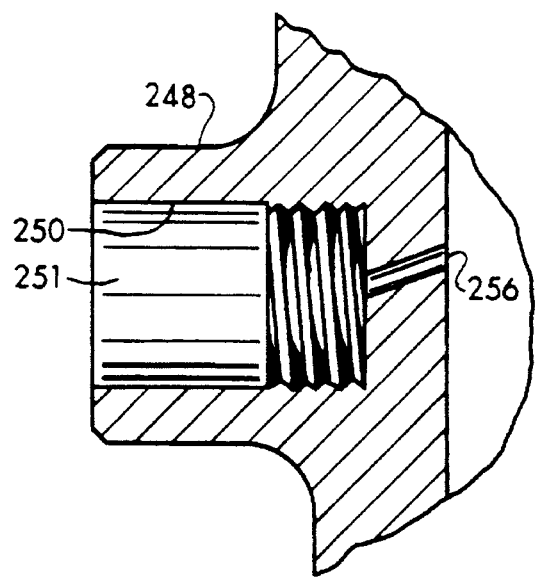
FIG. 8 is a cross section through the first bucket valve socket shown in FIG. 7, from proximal to distal.
Figure 9:
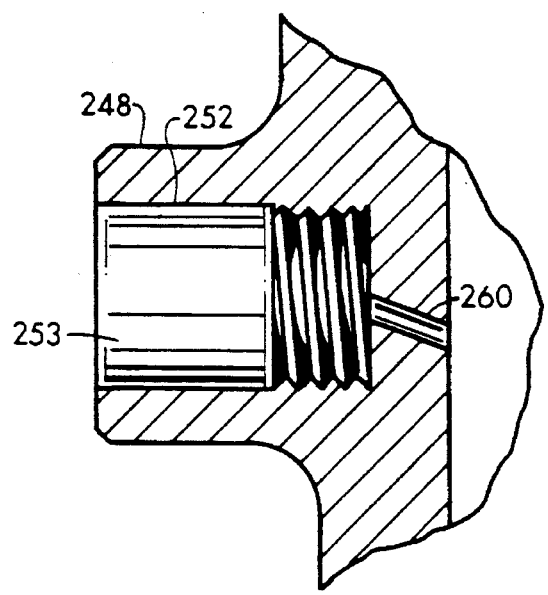
FIG. 9 is a cross section through the second bucket valve socket shown in FIG. 7, from proximal to distal.

At the proximal end of bucket 214, two pivot pins on the rotor arm (not shown) fit into recesses 244 in a proximal flange 246. A distal flange 248 adjacent the spacer 220 contains first, second and third valve sockets 250, 252, and 254, as shown in FIG. 7. Valves 251, 253, and 255 are mounted in valve sockets 250, 252, and 254, respectively. As shown in FIGS. 8 and 9, a first passage 256 connects the first valve socket 250 with a proximal channel 258 formed about the circumference of spacer 220. Second passage 260 connects second valve socket 252 with a distal circumferential channel 264 in spacer 220. Although not illustrated, third passage 262 connects third valve socket 254 with channel 264. A distal bore 266 through the interior of spacer 220 connects channel 264 and fluid collection chamber 238.

Figure 10:
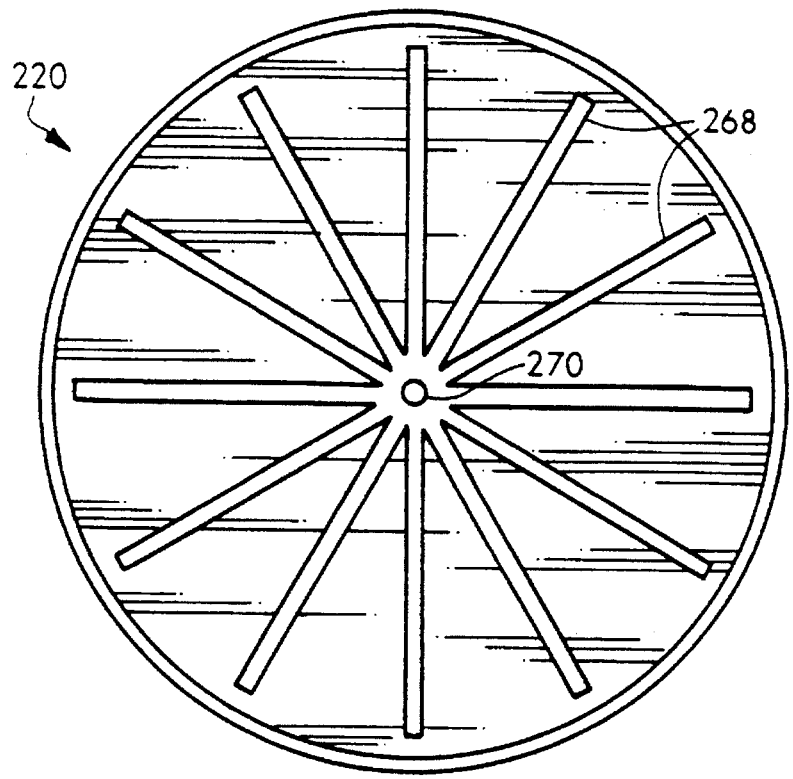
FIG. 10 is a view of the proximal surface of a spacer in the centrifuge bucket assembly of FIG. 1.
Figure 11:
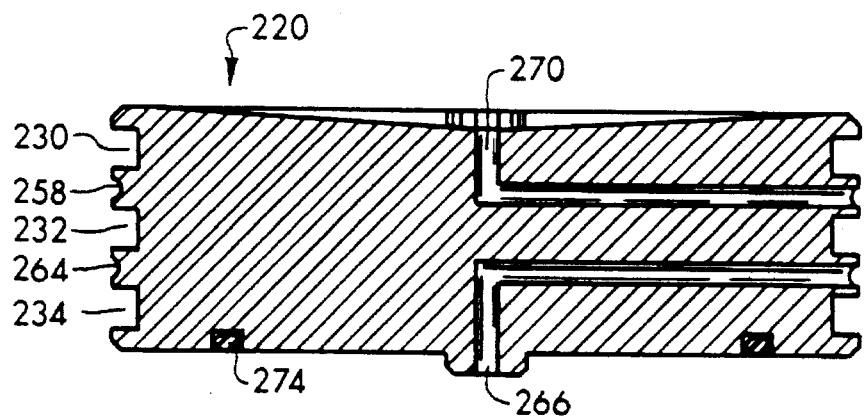
FIG. 11 is a cross section through the spacer of FIG. 5, from the proximal surface of the spacer to the distal surface.

FIG. 10 shows the proximal surface of spacer 220, and FIG. 11 is a cross section from the proximal surface to the distal surface through the center of the spacer. The proximal surface is angled so that the plate is thicker at its outer circumference than at its center. Grooves 268 in the proximal surface terminate at a proximal bore 270 which connects the proximal channel 258 to core chamber 236. A means 272 for attaching a fluid line is mounted in proximal bore 270 in spacer 220. O-rings 224, 226, and 228 between spacer 220 and the interior wall of the bucket provide seals between first and second channels 258 and 264, between spacer 220 and core chamber 236, and between spacer 220 and fluid collection chamber 238, respectively. O-ring 274 provides an additional seal between spacer 220 and fluid collection vessel 242.

Referring to FIG. 6, fluid collection vessel 242 fits inside the distal portion of the bucket 214. A hole 276 through the distal end of bucket 214 facilitates assembly and disassembly of vessel 242, spacer 220, and bucket 214.

In the cap, a fourth valve assembly 280 containing a valve 281 is mounted in fourth valve socket 282 and provides a fourth fluid passage through cap 212. A fifth valve assembly 284 containing a valve 285 is mounted in fifth valve socket 286 and provides a fifth fluid passage through cap 212. Alternatively, valve assemblies 280 and 284 and valves 281 and 285 could be mounted in the wall of bucket 214, rather than in cap 212.

The apparatus of FIGS. 6–12 may be used in the process of the present invention. Fluid collection vessel 242 and spacer 220 are placed inside centrifuge bucket 214. A core sample is saturated with a core saturating fluid and inserted into an overburden sleeve capable of attachment to fluid lines to provide fluid flow through the enclosed core. Fluid communication is then established, such as with hollow tubing, between fifth valve assembly 286 and the proximal end of the core sample and between the distal end of the core sample and means 272 in spacer 220. The core and sleeve are placed inside core chamber 236, and cap 212 is secured onto bucket 214. Valves 251, 253, 255, 281, and 285 are initially closed.

Outside the bucket, valve 281 is connected to an overburden fluid source and opened. The overburden fluid is supplied via valve 281 to the outside of the sleeve at a pressure greater than the bubble point of the core flooding fluid. Valve 281 is closed, and valve assembly 280 and bucket 214 are disconnected from the overburden source.

A replacement fluid source is then connected to valve 255. Valve 255 is then opened, thereby establishing a fluid flow path between the replacement fluid source and fluid collection chamber 238. A core flooding fluid source is connected to valve 285, and a receptacle for the core saturating fluid is connected to valve 251. Valve 285 is opened, establishing a fluid flow path for core flooding fluid between the core flooding fluid source and the saturating fluid receptacle through the core sample, proximal bore 270, and proximal channel 258.

The core flooding fluid is pumped through the core sample from the flooding fluid source, thereby replacing the core saturating fluid in the core sample. The saturating fluid then flows from the core and collects in grooves 268 in spacer 220. The saturating fluid flows through proximal bore 270 in spacer 220, proximal circumferential channel 258, proximal passage 256 and valve 251 to the saturating fluid receptacle. As the core flooding fluid flows through the core sample, the fluid pressures in core chamber 236 and fluid collection chamber 238 are simultaneously increased to the desired reservoir simulation pressure, which is preferably a pressure greater than the bubble point of the core flooding fluid and less than the overburden pressure in the reservoir. Several pore volumes of core flooding fluid oil are allowed to flow through the core sample and completely replace the core saturating fluid in the core. Then valves 251, 255, and 285 are closed. The core flooding fluid source and the saturating fluid receptacle are disconnected from valves 285 and 251, and the replacement fluid source is disconnected from valve 255.

After the core sample is saturated with core flooding fluid and the fluid collection chamber 238 is charged with the replacement fluid, a fluid flow connection is placed outside the bucket between valve 255 and valve 285. Another fluid flow connection is placed between valve 251 and valve 253. Valves 251, 253, 255, and 285 are opened, establishing a fluid flow loop encompassing the core sample and fluid collection chamber 238.

The bucket 214 is then placed in the centrifuge and spun. As a result of simulated gravity displacement, replacement fluid flows from the fluid collection vessel 242 in a proximal direction, through distal bore 266, distal channel 264, valve 253, and valve 251 into the core sample, where it replaces some of the core saturating fluid. Simultaneously, the replaced saturating fluid flows in a distal direction from the core sample through proximal bore 270 to the fluid collection vessel 242. The volume of fluid in the vessel can be determined by shining a light through windows 240 and the fluid collection vessel 242 and reading the fluid level from the graduations 278 on the fluid collection vessel.

As shown in FIGS. 6–12, core chamber 236 is proximal relative to fluid collection chamber 238, cap 212 is at the proximal end of bucket 214, and the distal end of bucket 214 is closed. It should be apparent to those skilled in the art that, depending on the nature of the core flooding fluid, the replacement fluid, and the fluid replacement process being simulated, the core chamber could be distal relative to the collection chamber. The open end of the bucket and the cap could be distal. Alternatively, the closed end of the bucket could be distal and have two valve assemblies mounted therein, and there could be no valve assemblies mounted in the cap.

The strength of the materials from which the bucket assemblies 10 and 210 are made limit the maximum internal pressure to which they can be subjected. The buckets 20 and 214, caps 50 and 210, spacer 220, and core holder 60 may be composed of any material which is capable of withstanding the internal pressure and temperature to which the bucket assembly will be subjected. The strength of the bucket and cap can be increased by increasing the wall thickness. However, the maximum outer dimensions which the centrifuge can accommodate and the minimum acceptable diameter of the core sample holder limit the maximum bucket wall thickness. Similarly, the maximum temperature at which the bucket can be used is limited by the maximum temperature at which the component materials will perform adequately.

Fluid collection vessels 120, 130, and 242 may be made from any material which can withstand the intended internal temperature and pressure. Examples of suitable materials are polyethersulfone, polysulfone, sapphire, and quartz. For example, a plastic such as polyethersulfone is suitable for pressures up to about 2000 psi and temperatures up to about 275° F. Sapphire would be suitable for pressures up to about 6000 psi and temperatures up to 400° F. Preferably, the vessel or vessels are transparent so that fluid levels can be observed optically within the vessel or vessels while they are inside the bucket. Observations can be made at any electromagnetic wavelength at which the vessel or vessels are transparent. Preferably, the wavelength is in the visible range. The fluid collection vessel or vessels may have graduations marked on the interior or exterior surfaces for the purpose of measuring the fluid volumes.

As will be apparent to one skilled in the art, the present invention can be used with any core holder which will fit inside the bucket. The core holder may be of a type other than an overburden sleeve.

While the foregoing preferred embodiments of the inventions have been described and shown, it is understood that the alternatives and modifications, such as those suggested and others, may be made thereto and fall within the scope of the invention.

I claim:

1. An apparatus for studying fluid replacement in core samples, the apparatus comprising:

(a) a bucket for use in a centrifuge, the bucket having an open proximal end, a distal end wall, a distal multiple valve assembly mounted in a distal valve socket in the end wall, a distal collection vessel in fluid communication with the distal valve socket, and a proximal collection vessel;

(b) an end cap capable of being secured to the proximal end of the centrifuge bucket, the cap having a proximal multiple valve assembly mounted in a proximal valve socket in the cap and a passage providing fluid communication between the proximal valve socket and the proximal collection vessel;

(c) a core sample holder for containing a core sample while applying an overburden pressure to the core sample and capable of being placed inside said bucket so that the core sample has a proximal end in fluid communication with the proximal collection vessel, the proximal fluid collection vessel sealingly mounted substantially between the core sample holder and the end cap, and a distal end in fluid communication with the distal collection vessel, the distal fluid collection vessel sealingly mounted substantially between the core sample holder and the distal end wall of the bucket; and (d) means for supplying overburden pressure to said core holder;

the apparatus capable of operation under conditions simulating subsurface hydrocarbon reservoir conditions, including fluid compositions, temperature, fluid pressure, and overburden pressure.

2. An apparatus for studying fluid replacement in core samples, the apparatus comprising:

(a) a bucket for use in a centrifuge, the bucket having an open proximal end, a distal end wall, a distal multiple valve assembly mounted in a distal valve socket in the end wall, a distal collection vessel in fluid communication with the distal valve socket, and a proximal collection vessel;

(b) an end cap capable of being secured to the proximal end of the centrifuge bucket, the cap having a proximal multiple valve assembly mounted in a proximal valve socket in the cap and a passage providing fluid communication between the proximal valve socket and the proximal collection vessel;

(c) a core sample holder for containing a core sample while applying an overburden pressure to the core sample and capable of being placed inside said bucket so that the core sample has a proximal end in fluid communication with the proximal collection vessel and a distal end in fluid communication with the distal collection vessel, said core sample holder comprises an outer wall, a core drain cap, a distal end plate, a resilient sleeve, an annulus between the outer wall and the sleeve, and a valve for introducing a fluid at overburden pressure into the annulus and maintaining pressure within the annulus; and (d) means for supplying overburden pressure to said core holder;

the apparatus capable of operation under conditions simulating subsurface hydrocarbon reservoir conditions, including fluid compositions, temperature, fluid pressure, and overburden pressure.

3. The apparatus of claim 2 wherein said valve in said core holder has an exterior surface and comprises an O-seal screw and said means for supplying overburden pressure to said core holder comprises a plurality of plates capable of being assembled around the exterior surface of said core holder, a set screw penetrating one of the plates and equipped with a screw driver end for turning the O-seal screw, one of the plates having a passage therethrough for providing a fluid under pressure to said valve in said core holder, and seals to prevent fluid leakage from the passage to the exterior of said core holder.

4. The apparatus of claim 3 wherein said proximal and distal collection vessels are transparent and said bucket additionally comprises at least one pair of opposing transparent windows adjacent each collection vessel.

5. An apparatus for studying fluid replacement in core samples, the apparatus comprising:

(a) a bucket for use in a centrifuge, the bucket having an open proximal end, a distal end wall, a distal multiple valve assembly mounted in a distal valve socket in the end wall, a distal collection vessel in fluid communication with the distal valve socket, and proximal collection vessel;

(b) an end cap capable of being secured to the proximal end of the centrifuge bucket, the cap having a proximal multiple valve assembly mounted in a proximal valve socket in the cap and a passage providing fluid communication between the proximal valve socket and the proximal collection vessel;

(c) a core sample holder for containing a core sample while applying an overburden pressure to the core sample and capable of being placed inside said bucket so that the core sample has a proximal end in fluid communication with the proximal collection vessel and a distal end in fluid communication with the distal collection vessel, wherein said collection vessels are made from a material selected from the group consisting of ployethersulfone, polysulfone, quartz, and sapphire; and (d) means for supplying overburden pressure to said core holder;

the apparatus capable of operation under conditions simulating subsurface hydrocarbon reservoir conditions, including fluid compositions, temperature, fluid pressure, and overburden pressure.

6. The apparatus of claim 1 wherein said bucket, end cap, and core holder are capable of operation inside said centrifuge at a temperature up to about 400° F.

7. The apparatus of claim 1 wherein said bucket, end cap, and core holder are capable of operation inside said centrifuge at a pressure up to about 6000 psi.

* * * * *